United States Patent [19]

Chase

[11] 4,401,441
[45] Aug. 30, 1983

[54] DIGESTER

[75] Inventor: Gregory J. Chase, West Brookfield, Mass.

[73] Assignee: Chase Precast Corp., North Brookfield, Mass.

[21] Appl. No.: 327,210

[22] Filed: Dec. 3, 1981

[51] Int. Cl.³ .......................... C12M 1/00; A01C 3/02
[52] U.S. Cl. ...................................... 48/111; 210/180;
  210/613; 422/240; 422/241; 435/313; 435/315;
  435/316
[58] Field of Search ...................... 48/111, 197 A, 209;
  210/180, 613, 603, 608; 435/313, 315, 316, 167,
  166; 422/240, 241; 52/404

[56] References Cited

U.S. PATENT DOCUMENTS

| | | | |
|---|---|---|---|
| 1,777,449 | 10/1930 | Rath | 201/45 |
| 3,981,803 | 9/1976 | Coulthard | 210/180 |
| 4,002,438 | 1/1977 | Fleming | 48/76 |
| 4,005,994 | 2/1977 | Feldmann | 48/111 |
| 4,053,395 | 10/1977 | Switzgable | 210/613 |
| 4,057,401 | 11/1977 | Boblitz | 48/111 |
| 4,058,948 | 11/1977 | Warren | 52/404 |
| 4,063,903 | 12/1977 | Beningson et al. | 44/2 |
| 4,098,040 | 7/1978 | Riefler | 52/404 |
| 4,100,023 | 7/1978 | McDonald | 435/167 |
| 4,152,122 | 5/1979 | Feldmann | 48/111 |
| 4,274,838 | 6/1981 | Dale et al. | 48/111 |
| 4,334,997 | 6/1982 | Peterson | 210/603 |

FOREIGN PATENT DOCUMENTS 2470159 6/1981 France .............................. 435/167

Primary Examiner—Peter F. Kratz
Attorney, Agent, or Firm—Blodgett & Blodgett

[57] ABSTRACT

Digester for producing organic material having a reaction chamber through which organic material is allowed to flow from an inlet opening to an outlet opening, having means for heating the organic material in the reaction chamber, and having means for collecting the fuel gas which is generated within the reaction chamber. The reaction chamber is located in a housing which has a continuous concrete wall within which is located a core of thermal insulating material to form a continuous insulating envelope around the reaction chamber.

7 Claims, 4 Drawing Figures

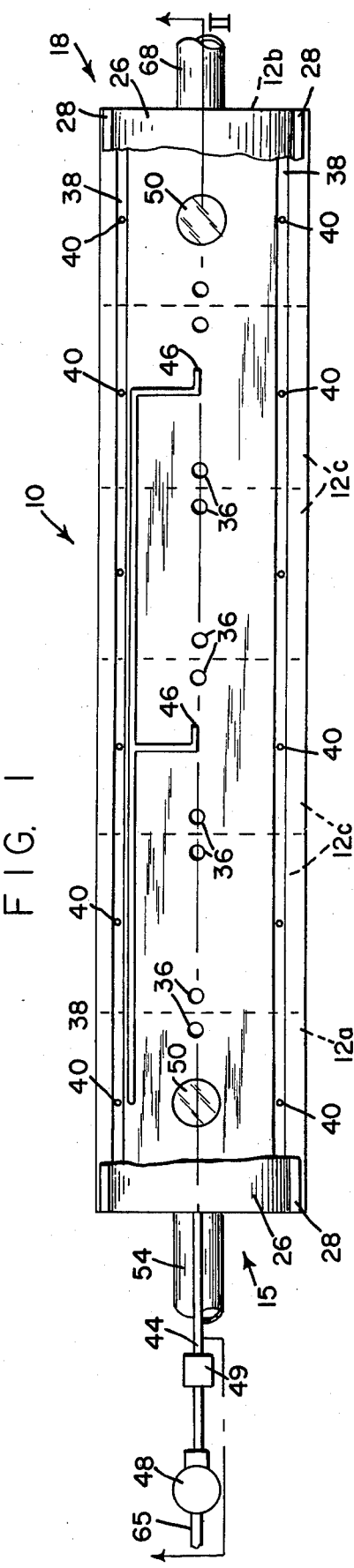
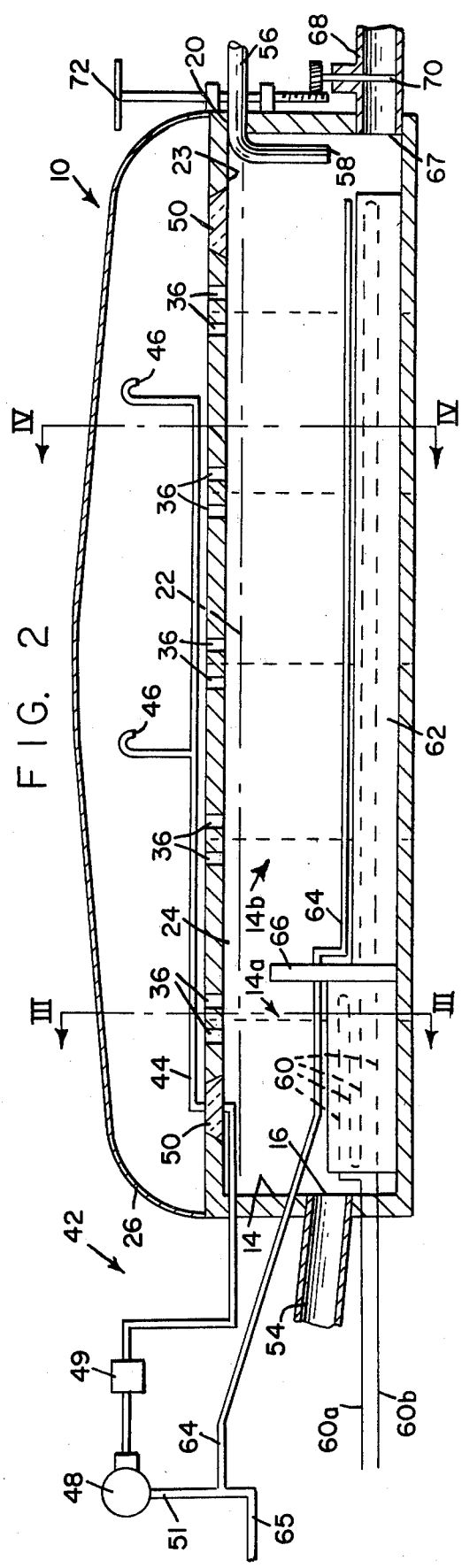

DIGESTER

BACKGROUND OF THE INVENTION

This invention relates generally to apparatus for digesting organic material to produce a fuel gas or biogas. More specifically, the invention is directed to a type of digester which has an elongated reaction chamber with an inlet opening, an outlet opening, and means for collecting the gas which is produced in the reaction chamber. Flowable organic material is fed into the reaction chamber through the inlet opening, flows through the chamber toward the outlet opening, and passes out of the chamber through the outlet opening. As the organic material flows through the reaction chamber between the inlet and outlet openings, it is digested by anaerobic or aerobic action to produce a fuel gas or biogas, such as methane mixed with $CO_2$.

Digesters of the type described above are generally constructed of concrete, since this material is relatively inexpensive, non-corrosive and long-lasting. The digester is constructed by assembling the digester at the site from precast concrete sections. It is also common practice to heat the digester to accelerate the microbial digestion.

One of the problems encountered in use of concrete for the construction of digesters is, that this material has very poor thermal insulating value. Therefore, much of the fuel which is collected from the digestion process is used for maintaining the temperature of the digester. This seriously effects the efficiency of the digester.

Attempts have been made in the past to insulate the digester by lining the inside or the outside surface of the digester. In either case, the insulation must be frequently replaced since those materials which have good thermal insulating qualities do not usually have good wear qualities and the wearing process further reduces the R-valve of the insulation. Another problem frequently encountered in the operation of digester systems is that the organic material has a tendency to form a crust at the top surface. This crust prevents gas which is generated in the organic material from passing out of the material to be collected. Also, the crust reduces the active area for digestion to take place. These and other difficulties experienced with the prior art devices have been obviated in a novel manner by the present invention.

It is, therefore, an outstanding object of the invention to provide a digester for producing fuel gas from organic material, which digester has a higher operating efficiency than the known prior art digesters.

Another object of this invention is the provision of a digester having a construction which combines strength and durability with high thermal insulation.

A further object of the present invention is the provision of a digester in which the organic material is constantly agitated to prevent crusting at the upper surface of an organic material.

It is another object of the instant invention to provide a digester in which the organic material is agitated by means of some of the gas which is generated from the material.

A still further object of the invention is the provision of a digester in which the organic material is heated, while the flow of organic material is resisted by means of a baffle to enable the material in the upstream side of the baffle to be properly heated.

A further object of the invention is to provide a digester in which a small space is created between the upper level of the organic material and the top of the digestion chamber to receive gas which is generated from the organic material.

It is a further object of the invention to provide a digester which includes a collection chamber located above the digester chamber and which includes means for conveying generated gas from the digestion chamber to the collection chamber.

It is a further object of the invention to provide a digester which is simple in construction, which is inexpensive to manufacture, and which is capable of a long life of useful service with a minimum of maintenance.

It is a further object of the invention to provide a digester which can be cleaned periodically with a minimum of effort.

With these and other objects in view, as will be apparent to those skilled in the art, the invention resides in the combination of parts set forth in the specification and covered by the claims appended hereto.

SUMMARY OF THE INVENTION

In general, the invention consists of a digester for producing fuel gas from organic material. The digester has a concrete housing which defines an elongated horizontal reaction chamber with an inlet opening at one end for receiving flowable organic material and with an outlet opening at the opposite end through which the organic material is removed. The housing has a continuous concrete wall with a continuous core of thermal insulating material embedded within the wall to form a continuous insulating envelope around the reaction chamber, while means is provided for collecting the fuel gas which is generated within the reaction chamber.

More specifically, a collection chamber is located above the reaction chamber and is operatively connected to the reaction chamber by venting means and a pump is provided for removing the gas from the collection chamber.

BRIEF DESCRIPTION OF THE DRAWINGS

The character of the invention, however, may be best understood by reference to one of the structural forms, as illustrated by the accompanying drawings, in which:

FIG. 1 is a plan view of a digester embodying the principles of the present invention with portions broken away, FIG. 2 is a vertical sectional view of the digester taken on the line II—II of FIG. 1.

DESCRIPTION OF THE PREFERRED EMBODIMENT

Figure 3:
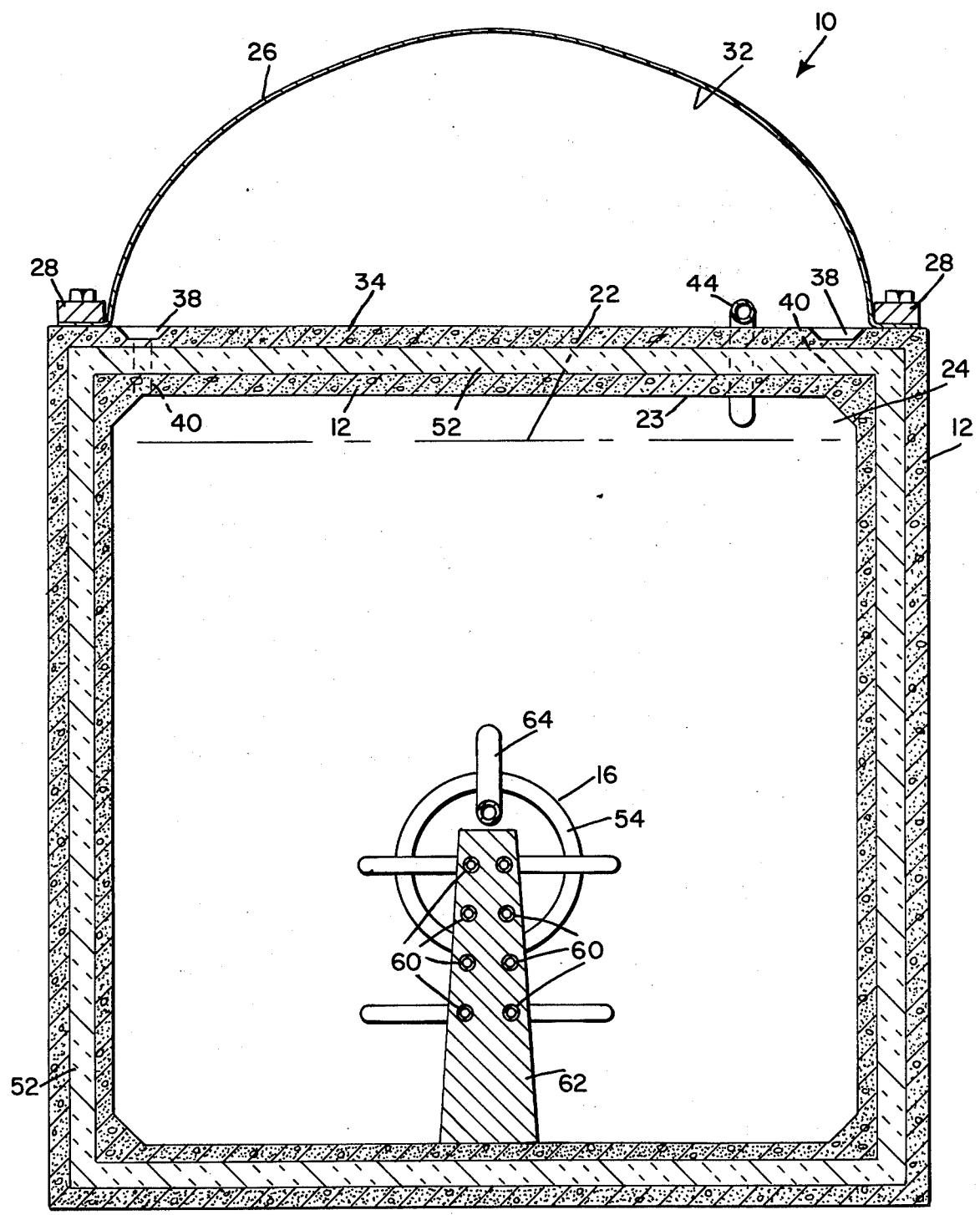
FIG. 3 is a vertical sectional view of the digester taken on the line III—III of FIG. 2.

Referring first to FIGS. 1 and 2, which best show the general features of the invention, the digester, indicated generally by the reference numeral 10, includes a concrete housing 12 which defines a reaction chamber 14. The front of the housing 12 is generally indicated by the reference numeral 15 and includes an inlet opening 16 for receiving flowable organic material. The back end of the housing is generally indicated by the reference numeral 18 and contains an outlet opening 20 which enables the organic material to flow through the reaction chamber through the outlet opening 20. The outlet opening 20 is located near the upper surface 23 of the reaction chamber 14, so that the chamber must be nearly filled with organic material before the material begins to pass out of the chamber through the outlet opening 20. In this way, the upper level of the organic material in the reaction chamber 14 never drops below the dot-and-dash line 22, indicated in FIG. 2. By feeding organic material into the reaction chamber 14 at the same rate at which it can leave the chamber through the outlet opening 20, the level of the organic material in the chamber is maintained at the upper level 22. Therefore, there is always a small space 24 between the upper level 22 and the upper surface 23 of the chamber. This enables gas which is generated in the organic material to pass from the organic material into the space 24.

Figure 4:
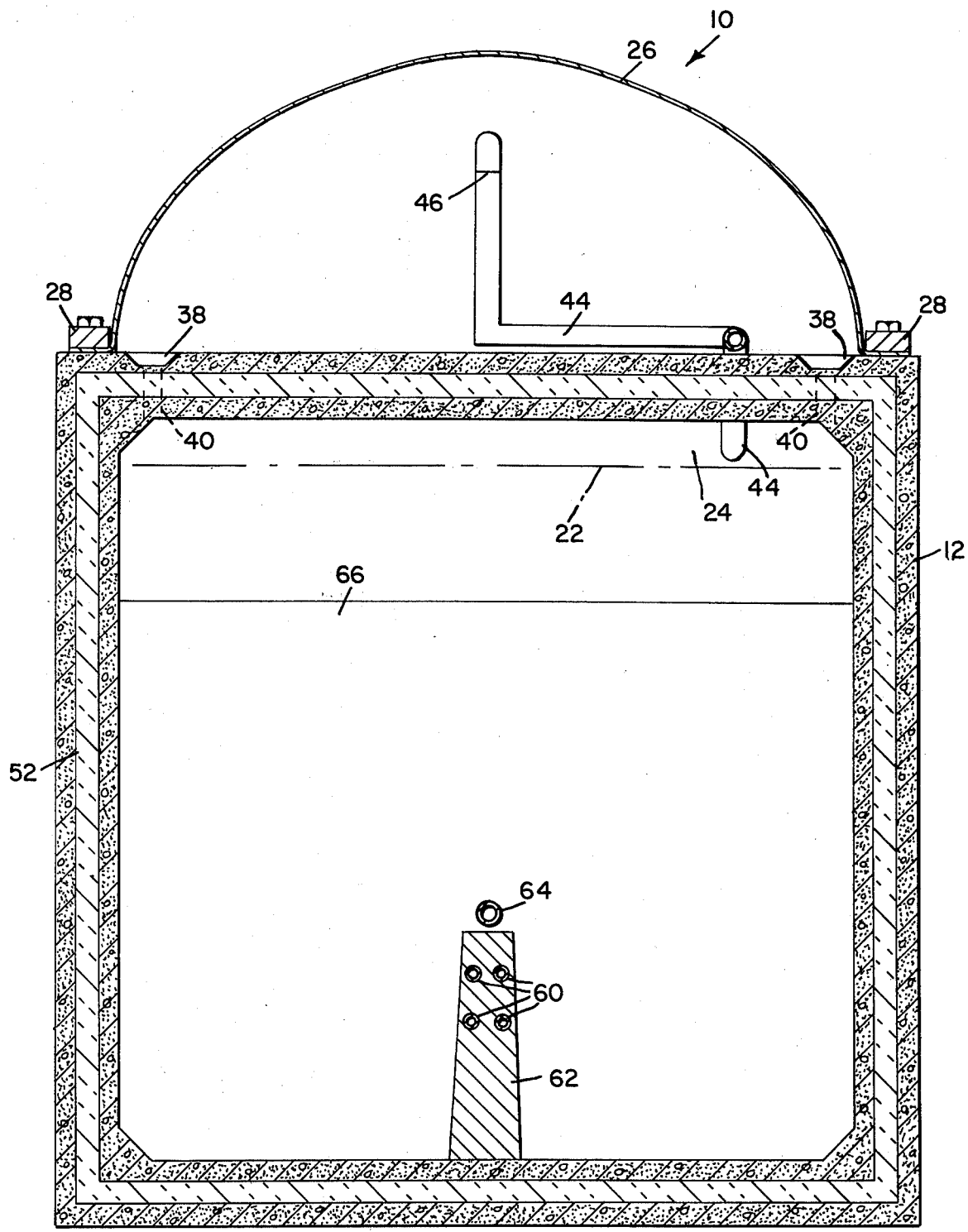
FIG. 4 is a vertical sectional view of the digester taken on the line IV—IV of FIG. 2.

A bag 26 consisting of flexible material is mounted on the housing 12 by means of clamping bars 28 located on opposite sides of the housing (see also FIGS. 3 and 4). The bag 26 defines a collection chamber 32 when it is expanded. The upper portion of the housing 12, indicated at 34, also defines the bottom boundary of the collection chamber 32 and contains a plurality of vent holes 36 which enables the gas which is generated in the organic material to pass into the collection chamber 32 from the space 24 at the top of the reaction chamber 14.

As shown in FIGS. 1-4, there is a trench 38 in the upper surface of the housing 12 at each side of the housing which extends along the entire length of the housing. A plurality of weep holes 40 extend downwardly from each trench 38 to the reaction chamber 14. This enables any condensation which collects on the inside surface of the bag 26 to run down the sides of the bag into the trenches 38 and to drain into the housing 14 through the drainage holes 40.

Referring particularly to FIGS. 1 and 2, the digester 10 includes pumping means, indicated by the reference numeral 42, which comprises a pipe 44 and a pump 48. The pipe 44 is located in the collection chamber 32 and has a plurality of openings 46 which enables gas which has accumulated in the collection chamber 32 to be drawn through the pipe by the pump 48 and pumped through a pipe 51 to be ultimately used as a fuel gas. Preferably, the gas which is drawn out of the collection chamber 32 passes through a flame trap 49 before reaching the pump 48. The upper portion 34 of the housing 16 is provided with an inspection window 50 at each end of the housing. Each inspection window 50 consists of clear or transparent material which provides for visual inspection of the interior of the reaction chamber 14.

Referring particularly to FIGS. 3 and 4, the housing 12 consists of a continuous concrete wall which is provided with a continuous core of thermal insulation material 52 which forms a continuous insulating envelope around the entire reaction chamber 14. The insulated wall construction shown in FIGS. 3 and 4 can be formed in one of at least two ways. One way is to position the insulating material 52 in a form, so that it is continuous except for one end. Concrete is then poured into the form so that it completely surrounds the insulating material except for an exposed edge at one end. This forms a complete reaction chamber housing except that the housing is open at this one end. The next step is to form an end wall which has a central core of insulating material so that the material is exposed along a continuous line which extends along one flat face of the end wall adjacent the outer edge of the wall. This end wall is then applied to the open end of the partially formed housing so that the exposed insulating edges of insulated material of the end wall and the partially formed portion of the housing engage so as to form a continuous envelope of insulating material. The end wall is preferably applied to the partially formed housing before the concrete has completely cured or is fastened to the housing by means of an adhesive material together with reinforcing plates. It is also possible to make the entire housing from a plurality of precast wall sections in which the portion of each section which abuts another section has an exposed edge of insulating material. When the two sections are joined, the exposed edges of insulating material of one section abuts the exposed edge of insulating material of the other section. When all of the sections are joined to form a complete housing a continuous envelope of insulating material is formed.

In the embodiment shown in FIGS. 1 and 2, the housing 12 is constructed of a plurality of precast sections. These sections consists of two end sections 12a, 12b and a plurality of intermediate sections 12c. The end section 12a forms the front end 15 of the housing and the end section 12b forms the back section 18 of the housing. Each of the end sections 12a and 12b is open at one end. The intermediate sections 12c are open at both ends and join the open ends of the front end section 12a to the back end section 12b. This may be accomplished by use of a single intermediate section 12c or a plurality of intermediate sections, as shown in FIG. 1. The open end of each end section has an exposed continuous edge of insulating material and each intermediate section 12c has an exposed edge of insulating material at each open end. When all of these sections 12a, 12b and 12c are joined, as shown in FIG. 1, a continuous concrete wall is formed having a continuous insulating core and serving to define the reaction chamber 14. The length of the reaction chamber 14 is determined by the number of intermediate sections 12c which are used. In this way, the reaction chamber can be constructed with a length which meets the particular needs of a consumer. Although many types of insulating material can be used, excellent results have been obtained by using sheets of closed-cell polyurethane.

As shown particularly in FIG. 2, the organic material to be digested is introduced into the reaction chamber 14 through a pipe 54 which extends from the inlet opening 16. A pipe 56 extends into the outlet opening 20 and terminates in an open end 58 which is located at a point considerably below the outlet opening 20. The organic material enters the open end 58 of the pipe 56 and flows out of the reaction chamber 14 through the pipe 56 to a collecting point such as a lagoon, not shown. In this way, the material passing out of the reaction chamber 14 is always drawn from a point below the upper level 22 of the material, thus preventing clogging of the pipe 56 by floating debris which sometimes appears in the organic material.

Referring to FIGS. 2-4, a plurality of heating tubes 60 are located in the lower portion of the chamber 14 and extend substantially the entire length of the chamber in a support 62. Each heating tube 60 is designed for conveying a heated fluid or steam and comprises an input section 60a and a return section 60b, as shown in FIG. 2. The heating tube 60 are effective to heat the organic material within the chamber 14 to a temperature in the range from 95° to 160° F.

A gas pipe 64 is also located in the lower portion of the reaction chamber 14 and extends along the entire length of the chamber just above the support 62. The gas pipe 64 has a plurality of small apertures along its entire length and is connected to the pipe 51, so that some of the generated gas drawn from the collection chamber 32 by the pump 48 is returned to the reaction chamber 14. The gas bubbling up from the gas pipe 64 through the organic material in the reaction chamber 14 agitates the organic material into suspension and prevents crusting at the upper surface or level 22 of the material.

Referring to FIGS. 2 and 4, a baffle 66 extends across the entire width of the chamber 14 and extends upwardly from the lower surface of the chamber to a point substantially below the upper surface 23 of the chamber and below the upper level 22 of the organic material. Baffle 66 is located closer to the front end 15 and divides the reaction 14 into a forward section 14a and a rearward section 14b.

Referring particularly to FIG. 2, the back end 18 of the housing is provided with a drainage opening 67. A drainage pipe 68 is connected to the opening 67 and is provided with a gate 70 which can be mutually opened by a handle 72. The drainage pipe enables the entire reaction chamber 14 to be flushed out with water in the event that the system becomes clogged with segment sediment or other debris.

The operation and advantages of the present invention will now be readily understood in view of the above description. Assuming that chamber 14 is empty, organic material is fed into the chamber through the pipe 54. The forward section 14a is filled first and eventually the material flows over the top of the baffle 66 and begins to fill the rearward section 14b. The baffle 66 prevents the organic material entering the chamber 14 from surging toward the back end of the chamber before it has had a change to be heated. The baffle 66 insures that the material entering the chamber 14 is retained, at least temporarily, in the forward section 14a, so that it has a chance to be properly heated before flowing over the top of the baffle and into the rearward section 14b. In addition, each of the heating tubes 60 has an extra loop in the input line in the forward section 14a so as to further insure that the organic material is properly heated when it first enters the reaction chamber 14a. As organic material continually arrives through the inlet opening 16, the rearward section 14b of the reaction chamber fills up until the upper level of the material in the entire reaction chamber reaches the upper level 22. At this point, the organic material begins to flow out of the outlet opening 20 through the pipe 56. Since the opening 58 of the pipe 56 is located below the flow line 22, the organic material will flow out of the reaction chamber 14 from a point substantially below the upper flow line 22, so that floating debris at the surface is prevented from entering and clogging the pipe 56.

The envelope which is formed about the reaction chamber 14 by the continuous core of insulating material 52 within the continuous concrete wall of the housing 12 contributes greatly to the operating efficiency of the digester. Since the organic material within the reaction chamber 14 must be heated to maximize the production of gas by microbial action, a certain amount of energy is expended for the heating process. The operating efficiency of the entire digestive system depends on the amount of useable fuel which is collected by the system in comparison to the amount of fuel which is used for heating the organic material within the reaction chamber. If there is a great deal of heat loss through the wall of the reaction chamber, the operating efficiency of the digester is greatly reduced. Although concrete is poor thermal-insulating material, the core of insulating material 52 within the concrete walls of the housing 12 is effective in preventing heat escaping from the chamber 14 to the outside. It is also important that the insulating material be continuous except, of course, for the holes 36 and 40 including inspection manholes, so that a complete envelope of insulating material is formed about the reaction chamber 14. Even if the housing 12 were constructed of concrete slabs, each containing a core of insulating material and if there was no insulating material in the areas of the concrete wall where the slabs joined, there would be a considerable heat loss at the joining or abutting areas.

By the process of aerobic or anaerobic microbial action, gas is generated in the organic material in the reaction chamber 14. Gas which is generated in this way bubbles up through the organic material and enters the space 24 between the upper upper level 22 of the material and the upper surface 23 of the reaction chamber. This generated gas then enters the collection chamber 32 through the holes 36 in the upper portion 34 of the housing. The gas is then drawn out of the collection chamber 32 by the pump 48 and is then pumped into the pipe 51. Some of the gas from the pipe 51 enters the pipe 64 and the remainder of the gas from pipe 51 enters the pipe 54 where it is utilized for heating or power generation. The gas which enters the pipe 64 returns to the reaction chamber 14 and is released into the organic material in the chamber by means of the apertures in section of the pipe 64 which is located in the chamber. This released gas bubbles up through the organic material and agitates the material and prevents crusting at the surface of the material. If a crust were allowed to form at the surface of the organic material it would form a gas impervious barrier which would prevent gas which is generated in the material from passing into the space 24 and the collection chamber 32. Some of the generated gas which is pumped through the pipe 65 can be used for heating the fluid which is circulated to the heating tubes 60.

After a period of operation it may be desired to inspect the reaction chamber 14. This inspection may be prompted by an apparent diminishing of efficiency of the system or simply by a curiosity of the operator to see how the operation is proceeding. Prior to making such an observation, heating or organic material into the chamber is halted, all of the gas in the collection chamber 32 is pumped out and the entire system is shut down. The bag 26 is removed and the operator checks the condition of the reaction chamber 14 by looking through the inspection windows 50. In the event that the operator observes a substantial accumulation of sediment or non-digestable material in the chamber 14 which may be affecting the efficiency of the system, the operator may decide to perform a flushing operation. A flushing operation is performed by opening the gate 70 and introducing water into the reaction chamber 14 through the pipe 54. This operation continues until all of the sediment or other material is completely flushed out of the reaction chamber 14 through the drainage pipe 68. When the operator determines that the reaction chamber 14 is sufficiently cleaned, the rest of the water is allowed to drain out of the chamber through the drain pipe 68. The gate 70 is then closed and the bag 26 reapplied to the housing 12. Organic material is then introduced into the reaction chamber 14 until the chamber is filled, as described previously, and the entire system is activated in the manner previously described.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. Digester for producing fuel gas from organic material, said digester comprising:
   (a) a concrete housing which has a front end and a back end and which defines an elongated horizontal reaction chamber which extends from the front end to the back end, said housing having a continuous concrete wall with an inlet opening at the front end for receiving flowable organic material and an outlet opening at the back end through which said organic material is removed, enabling the organic material to flow through the chamber from the front end to the back end, said housing comprise a substantially closed, continuous inner layer of concrete; a substantially closed continuous intermediate layer of thermal insulating material; and a substantially closed, continuous outer layer of concrete; the housing thereby forming a substantially closed, continuous insulating envelope around the reaction chamber,
   (b) heating elements which extend substantially the entire length of the reaction chamber for heating the organic material in the reaction chamber,
   (c) means for collecting the fuel gas which is generated within the reaction chamber, and
   (d) a baffle located within the reaction chamber between said front and back ends, said baffle extending from the bottom and across the entire width of the reaction chamber, and being spaced from the top of the reaction chamber so that said organic material is forced to flow over the baffle as it flows from said front end to said back end, the baffle dividing the reaction chamber into a forward section toward the front end and a rearward section toward the back end, the said forward section being smaller in volume than the rearward section, and wherein said heating elements are located in both, said forward section and said rearward section.

2. Digester as recited in claim 1, wherein the outlet opening is located below the upper limit of the chamber so that there is a space between the organic material and the upper limit of the chamber, and wherein the means for collecting the fuel gas comprises:
   (a) a collection chamber located above the reaction chamber, the collection chamber having a bottom boundary defined by the portion of the wall of the housing between the collection chamber and the housing,
   (b) venting means operatively connecting the space to the collection chamber comprising a plurality of holes in said bottom boundary, and
   (c) pump means for removing the gas from the collection chamber for use.

3. Digester as recited in claim 2, wherein the collection chamber is formed by a flexible inflatable bag attached to the top of the housing.

4. Digester as recited in claim 1, wherein the said collecting means is a pump means, the digester further comprising:
   (a) an elongated pipe which is located within the reaction chamber along substantially the entire length of the chamber, said pipe having a plurality of holes along its length, and
   (b) return piping for connecting the pump means to the elongated pipe for returning a portion of the gas removed from the collection chamber to the elongated pipe to function as an agitating means to prevent crust formation.

5. Digester for producing fuel gas from organic material, said digester comprising:
   (a) a housing formed of discreet precast concrete sections which has a front end and a back end and which defines an elongated horizontal reaction chamber which extends from the front end to the back end, said housing having a continuous wall formed of said precast sections which are sealed at their adjacent edges, the housing having an inlet opening at the front end for receiving flowable organic material and an outlet opening at the back end through which said organic material is removed, enabling the organic material to flow through the chamber from the front end to the back end, said housing comprising a continuous core of thermal insulating material embedded within the continuous concreate wall to form a substantially closed, continuous insulating envelope around the reaction chamber,
   (b) means for collecting the fuel gas which is generated within the reaction chamber,
   (c) heating elements which extend substantially the entire length of the reaction chamber, and
   (d) a baffle located within the reaction chamber between said front and back ends, said baffle extending from the bottom and across the entire width of the reaction chamber, and being spaced from the top of the reaction chamber so that said organic material is forced to flow over the baffle as it flows from said front end to said back end, the baffle dividing the reaction chamber into a forward section toward the front end and a rearward section toward the back end, the said forward section being smaller in volume than the rearward section, and wherein said heating elements are located in both, said forward section and said rearward section.

6. Digester as recited in claim 5, wherein said housing comprises two precast end sections of box shape.

7. Digester as recited in claim 6, wherein the housing further comprises at least one precast intermediate section of box shape.

* * * * *